United States Patent
Bank et al.

(10) Patent No.: US 9,931,248 B2
(45) Date of Patent: Apr. 3, 2018

(54) NON-INVASIVE VISION ENHANCEMENT

(71) Applicant: INTERNATIONAL BUSINESS MACHINES CORPORATION, Armonk, NY (US)

(72) Inventors: Judith H. Bank, Morrisville, NC (US); Liam Harpur, Dublin (IE); Patrick J. O'Sullivan, Dublin (IE); Lin Sun, Morrisville, NC (US)

(73) Assignee: International Business Machines Corporation, Armonk, NY (US)

( * ) Notice: Subject to any disclaimer, the term of this patent is extended or adjusted under 35 U.S.C. 154(b) by 289 days.

(21) Appl. No.: 14/305,481

(22) Filed: Jun. 16, 2014

(65) Prior Publication Data
US 2015/0359681 A1 Dec. 17, 2015

(51) Int. Cl.
*A61F 9/08* (2006.01)
*G10L 15/08* (2006.01)
(Continued)

(52) U.S. Cl.
CPC ........... *A61F 9/08* (2013.01); *G02B 27/01* (2013.01); *G10L 15/08* (2013.01); *H04N 5/2258* (2013.01);
(Continued)

(58) Field of Classification Search
CPC .... A61F 9/08; A61F 2250/0085; G10L 15/22; G10L 15/08; G06F 3/0488;
(Continued)

(56) References Cited

U.S. PATENT DOCUMENTS 2,623,433 A * 12/1952 Stipek .................... G03B 35/20
353/8
6,204,974 B1 * 3/2001 Spitzer ................... G02C 7/086
359/630
(Continued)

FOREIGN PATENT DOCUMENTS

EP 1808722 A2 7/2007
EP 1808722 A3 7/2007
(Continued)

OTHER PUBLICATIONS

Wikipedia.com "Virtual retinal display" <http://en.wikipedia.org/wiki/Virtual_retinal_display> Mar. 2014. (6 Pages).
(Continued)

*Primary Examiner* — Sath V Perungavoor
*Assistant Examiner* — Philip Dang
(74) *Attorney, Agent, or Firm* — Tutunjian & Bitetto, P.C.; Ed Choi

(57) ABSTRACT

A method and system are provided for enhancing vision. The method includes capturing a first image by a first camera. The method further includes capturing a second image by a second camera. The method also includes combining the first image and the second image to form a combined image. The method additionally includes projecting the combined image on at least one eye of a user by a wearable image projection device. The combined image represents a wide screen image having a field of view greater than any of the first image and the second image taken individually.

14 Claims, 6 Drawing Sheets

(51) Int. Cl.
*G02B 27/01* (2006.01)
*H04N 5/225* (2006.01)
*H04N 7/18* (2006.01)
*G10L 15/22* (2006.01)
*H04N 5/232* (2006.01)

(52) U.S. Cl.
CPC ....... *A61F 2250/0085* (2013.01); *G10L 15/22* (2013.01); *H04N 5/23238* (2013.01); *H04N 7/181* (2013.01)

(58) Field of Classification Search
CPC ...... H04N 5/7491; H04N 5/265; H04N 7/181; H04N 5/2258; H04N 5/23238; G02B 27/01
See application file for complete search history.

(56) References Cited

U.S. PATENT DOCUMENTS

| | | | | |
|---|---|---|---|---|
| 6,384,982 B1* | 5/2002 | Spitzer | ................ | G02B 27/017 359/630 |
| 6,417,969 B1* | 7/2002 | DeLuca | ............ | G02B 27/2235 345/8 |
| 7,148,861 B2 | 12/2006 | Yelton et al. | | |
| 7,549,746 B2* | 6/2009 | Tsukada | ................ | A61B 3/102 351/206 |
| 7,973,750 B2* | 7/2011 | Miyazawa | ............ | G09G 3/002 345/690 |
| 7,982,777 B2 | 7/2011 | Prechtl et al. | | |
| 8,325,263 B2* | 12/2012 | Kato | ................... | G02B 27/017 345/8 |
| 8,467,133 B2* | 6/2013 | Miller | ................... | G02B 27/017 353/28 |
| 8,473,004 B2 | 6/2013 | Warren | | |
| 8,520,023 B2* | 8/2013 | Sullivan | ............... | G06T 11/001 345/589 |
| 8,567,953 B2* | 10/2013 | O'Dor | ................ | H04N 9/3147 250/205 |
| 2006/0087618 A1* | 4/2006 | Smart | ................... | A61B 3/005 351/222 |
| 2008/0170119 A1 | 7/2008 | McCann | | |
| 2008/0186604 A1 | 8/2008 | Amitai | | |
| 2008/0309884 A1* | 12/2008 | O'Dor | ................ | H04N 9/3147 353/7 |
| 2009/0051879 A1* | 2/2009 | Vitale | ................... | G03B 21/28 353/28 |
| 2010/0149073 A1 | 6/2010 | Chaum et al. | | |
| 2011/0085029 A1 | 4/2011 | Noguchi | | |
| 2011/0241976 A1* | 10/2011 | Boger | ................ | G02B 27/0172 345/8 |
| 2012/0218301 A1* | 8/2012 | Miller | ................ | G02B 27/017 345/633 |
| 2012/0249797 A1* | 10/2012 | Haddick | ................ | G06F 1/163 348/158 |
| 2013/0204881 A1* | 8/2013 | Su | ........................ | G06N 5/043 707/749 |
| 2013/0208234 A1 | 8/2013 | Lewis | | |
| 2013/0215235 A1* | 8/2013 | Russell | ............. | H04N 13/0203 348/47 |
| 2013/0307842 A1* | 11/2013 | Grinberg | ............... | G06F 3/1431 345/419 |
| 2014/0005485 A1* | 1/2014 | Tesar | ..................... | A61B 17/02 600/201 |
| 2014/0043352 A1* | 2/2014 | Damberg | ............. | H04N 9/3147 345/589 |
| 2014/0111421 A1* | 4/2014 | Fischer | ................ | G02B 27/017 345/156 |
| 2014/0160250 A1* | 6/2014 | Pomerantz | ......... | H04N 5/23229 348/47 |

FOREIGN PATENT DOCUMENTS

| | | |
|---|---|---|
| WO | WO9717043 A1 | 5/1997 |
| WO | WO9954778 A3 | 10/1999 |
| WO | WO2006015315 A2 | 2/2006 |

OTHER PUBLICATIONS

Balakrishnan, G., et al. "Wearable Real-Time Stereo Vision for the Visually Impaired" Engineering Letters, 14:2. May 2007. (9 Pages).

\* cited by examiner

NON-INVASIVE VISION ENHANCEMENT

BACKGROUND

Technical Field

The present invention relates generally to enhancing vision and, in particular, to non-invasive vision enhancement.

Description of the Related Art

There are many people who no longer have clear vision, or any vision in one eye. This can be caused by accident or disease. It is not always possible to improve or replace vision in the affected eye, which can hamper the user's ability to drive a vehicle or do certain types of work.

There have been a number of new appliances which restore vision by projecting video images onto a retina, but they require invasive implants. People that have distorted vision but are not totally blind in the affected eye might be reluctant to undergo invasive surgery on their eyes and/or brain and wear implanted devices.

SUMMARY

According to an aspect of the present principles, there is provided a method for enhancing vision. The method includes capturing a first image by a first camera. The method further includes capturing a second image by a second camera. The method also includes combining the first image and the second image to form a combined image. The method additionally includes projecting the combined image on at least one eye of a user by a wearable image projection device. The combined image represents a wide screen image having a field of view greater than any of the first image and the second image taken individually According to another aspect of the present principles, there is provided a system for enhancing vision. The system includes a first camera for capturing a first image. The system further includes a second camera for capturing a second image. The system also includes an image combiner for combining the first image and the second image to form a combined image. The system additionally includes a wearable image projection device for projecting the combined image on at least one eye of a user. The combined image represents a wide screen image having a field of view greater than any of the first image and the second image taken individually These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

Figure 1:
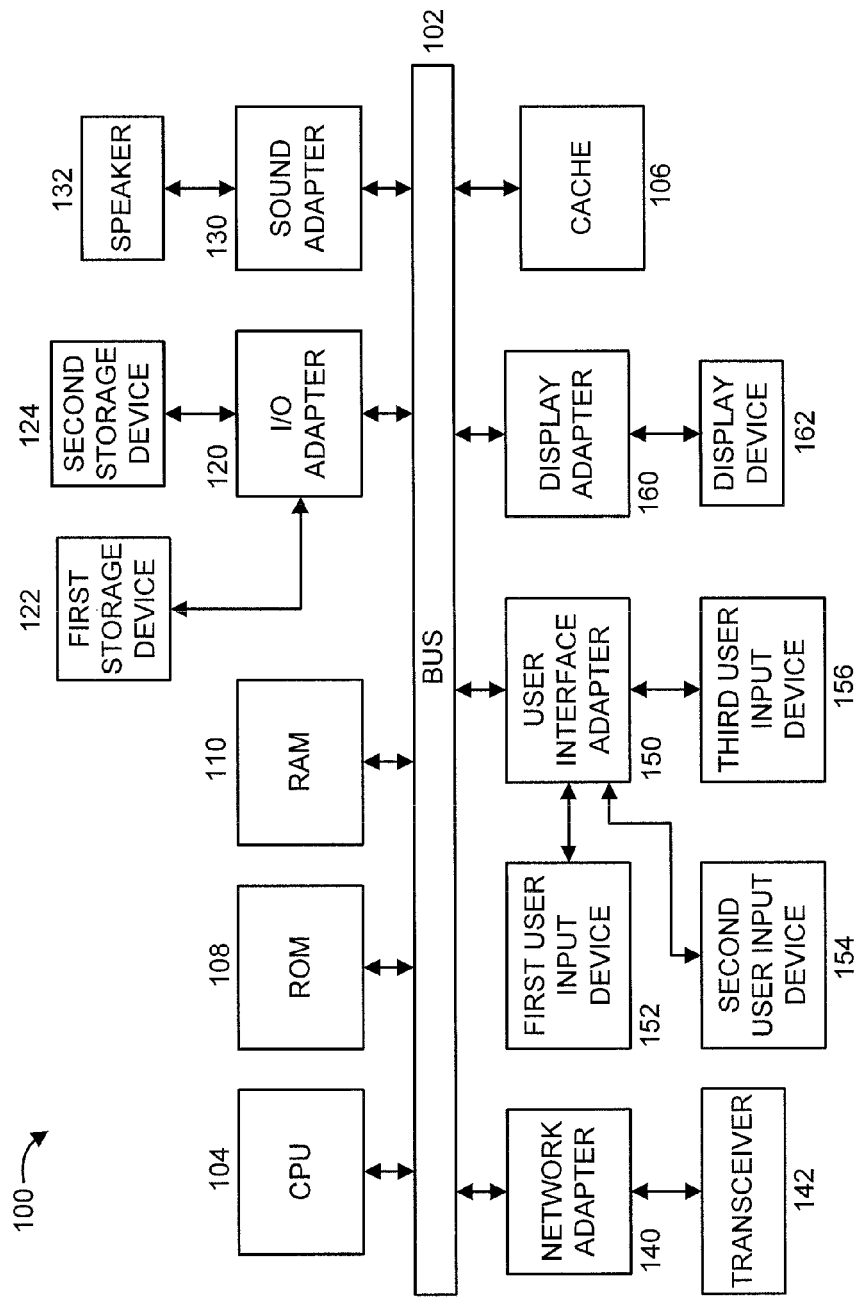
FIG. 1 shows an exemplary processing system 100 to which the present principles may be applied, in accordance with an embodiment of the present principles.

The present principles are directed to non-invasive vision enhancement.

Advantageously, the present principles provide a solution that avoids the use or need of implants and/or invasive surgery. The present principles can be applied to individuals having non-transient visual deficiencies as well as individuals suffering from temporary visual deficiencies including, but not limited to, impaired vision in one or both eyes.

In an embodiment, the present principles would involve capturing two video streams, one for each eye, and combining the two video streams into a single wide screen display which is directed to the good eye by an appliance built into special eyeglasses.

It is to be appreciated that there are multiple ways to implement the present principles. Moreover, given the teachings of the present principles provided herein, one of ordinary skill in the art will contemplate the implementation disclosed herein as well as various other implementations, while maintaining the spirit of the present principles.

A description will now be given of an illustrative embodiment of the present principles. The description will use terms such as "good" eye and "affected eye". The term "good eye" refers to the eye of an individual having better vision as compared to the "affected eye". The term "affected eye" refers to the eye of the individual that has the worse vision from among the individual's two eyes. In an embodiment, the vision of the affected eye is supplemented by providing enhanced vision to the "good eye" as described herein. It is to be appreciated that the term "good eye" is a relative term with respect to the term "affected eye" and, thus, the term "good eye" does not intend to connote an eye having perfect vision, but simply the eye having better vision than the "affected eye". Accordingly, in an embodiment, the vision of the good eye may be enhanced even in cases where the good eye provides less than optimal vision but nonetheless provides better vision than the affected eye.

In an embodiment, an eye tracking mechanism determines the user's field of vision and focus, and two video cameras capture images that would be seen by each eye. The images would be combined in real time and be displayed to the "good eye". This would allow the eye with better vision to see a wider view or to perceive correct depth by including the images which would have previously been seen in the peripheral vision field of the affected eye (eye before its vision was impaired).

Ordinarily the "good eye" focus point would be used to position the cameras, since the affected eye focus point may not be reliable. However, the user could also choose to track both eyes for camera positioning. In an embodiment, the present principles can also involve one or more of a speaker, microphone, a speech and/or speaker recognition system, and voice synthesis system to receive and interpret voice commands from the user and respond, if desired.

A user could input his eyeglasses prescription and adjust the device for any reasonable vision setting (e.g., a setting of 20/20) but could also enhance near or far vision (e.g., a setting of 20/15). This would be very convenient for precision work like assembling small components, and so forth. The vision system video component would compensate for the user's vision by adjusting the images to achieve the desired level of correction. The user could dynamically change the calibration, for example to see something farther down the road by speaking a command such as "increase distance".

When enhancing vision in the affected eye, to compensate for distortion (e.g., wavy images) the user could speak a command like "right eye straighten vertical lines" or "both eyes straighten horizontal lines" or "sharpen image" or "enlarge image". The vision enhancing system would attempt to adjust the video image(s) using clues from the user (e.g., "worse" or "better" or "OK now", etc.). Thus, for example if a straight object appeared to have an S curve, the vision system could use a backwards S filter to achieve a straighter view. For blurry vision, the vision system could increase the contrast. In other words, this process could be somewhat similar to the tuning of older TV sets via voice commands. The vision system could also simplify the image by displaying object outlines, similar to a line drawing. The system could also reduce glare (e.g., bright light or sunlight) if applicable by applying a darkening filter.

FIG. 1 shows an exemplary processing system 100 to which the present principles may be applied, in accordance with an embodiment of the present principles. The processing system 100 includes at least one processor (CPU) 104 operatively coupled to other components via a system bus 102. A cache 106, a Read Only Memory (ROM) 108, a Random Access Memory (RAM) 110, an input/output (I/O) adapter 120, a sound adapter 130, a network adapter 140, a user interface adapter 150, and a display adapter 160, are operatively coupled to the system bus 102.

A first storage device 122 and a second storage device 124 are operatively coupled to system bus 102 by the I/O adapter 120. The storage devices 122 and 124 can be any of a disk storage device (e.g., a magnetic or optical disk storage device), a solid state magnetic device, and so forth. The storage devices 122 and 124 can be the same type of storage device or different types of storage devices.

A speaker 132 is operative coupled to system bus 102 by the sound adapter 130. Moreover, the speaker 132 can be part of a speech synthesis system, with other parts of the system implemented entirely as one or more user input devices (described below) or implemented in other elements of system 100 including, but not limited to, CPU 104 and any of the memories.

A transceiver 142 is operatively coupled to system bus 102 by network adapter 140.

A first user input device 152, a second user input device 154, and a third user input device 156 are operatively coupled to system bus 102 by user interface adapter 150. The user input devices 152, 154, and 156 can be any of a keyboard, a mouse, a keypad, an image capture device, a motion sensing device, a microphone, a device incorporating the functionality of at least two of the preceding devices, and so forth. For items such as a keyboard, they are either preferably miniaturized or virtual. Moreover, the microphone can be part of a speaker recognition system and/or speech recognition system, with other parts of these systems implemented entirely as one or more user input devices or implemented in other elements of system 100 including, but not limited to, CPU 104 and any of the memories. Of course, other types of input devices can also be used, while maintaining the spirit of the present principles. The user input devices 152, 154, and 156 can be the same type of user input device or different types of user input devices. The user input devices 152, 154, and 156 are used to input and output information to and from system 100.

A display device 162 is operatively coupled to system bus 102 by display adapter 160.

Of course, the processing system 100 may also include other elements (not shown), as readily contemplated by one of skill in the art, as well as omit certain elements. For example, various other input devices and/or output devices can be included in processing system 100, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 100 are readily contemplated by one of ordinary skill in the art given the teachings of the present principles provided herein.

Figure 2:
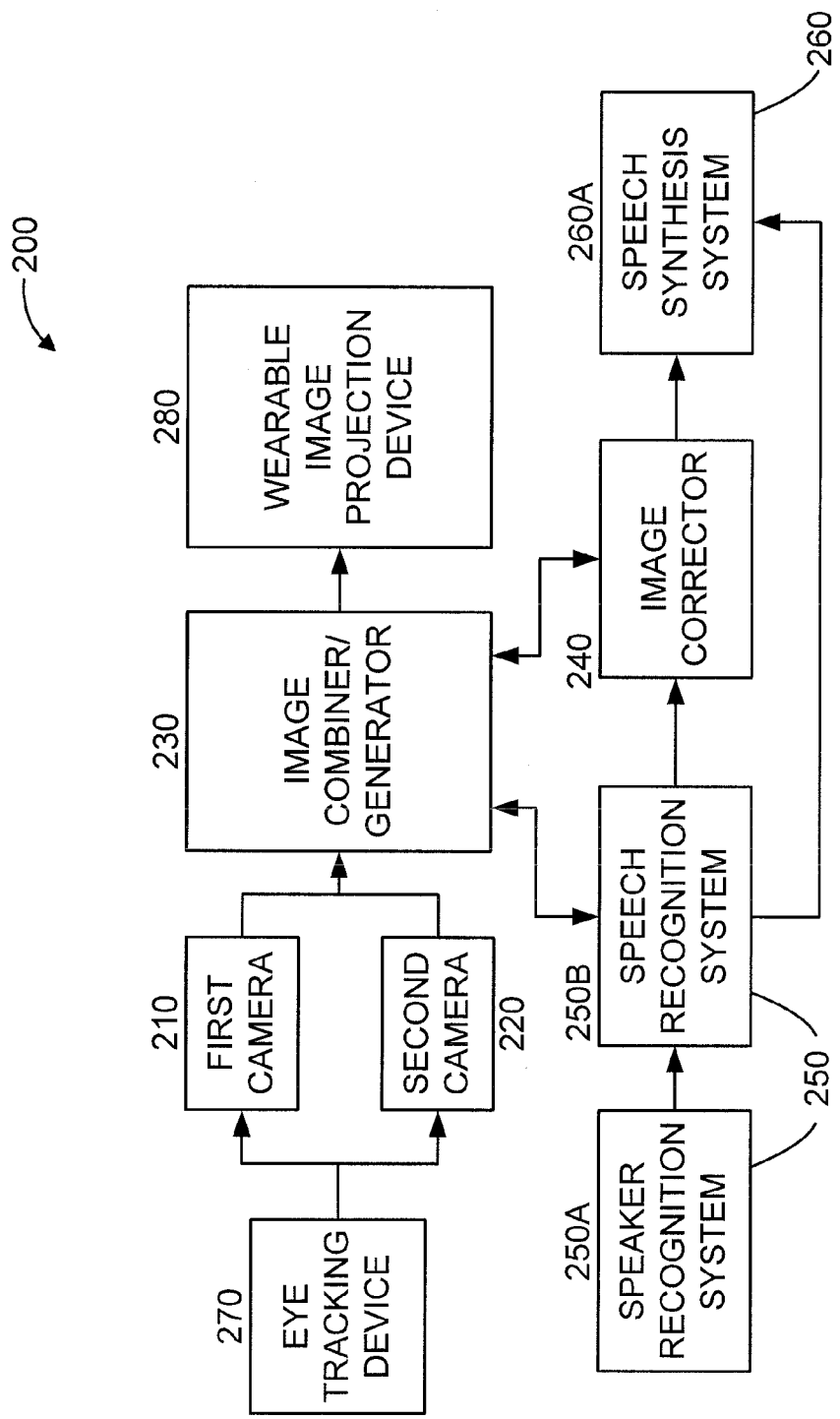
FIG. 2 shows an exemplary system 200 for enhancing vision, in accordance with an embodiment of the present principles.

Moreover, it is to be appreciated that system 200 described below with respect to FIG. 2 is a system for implementing respective embodiments of the present principles. Part or all of processing system 100 may be implemented in one or more of the elements of system 200.

Figure 3:
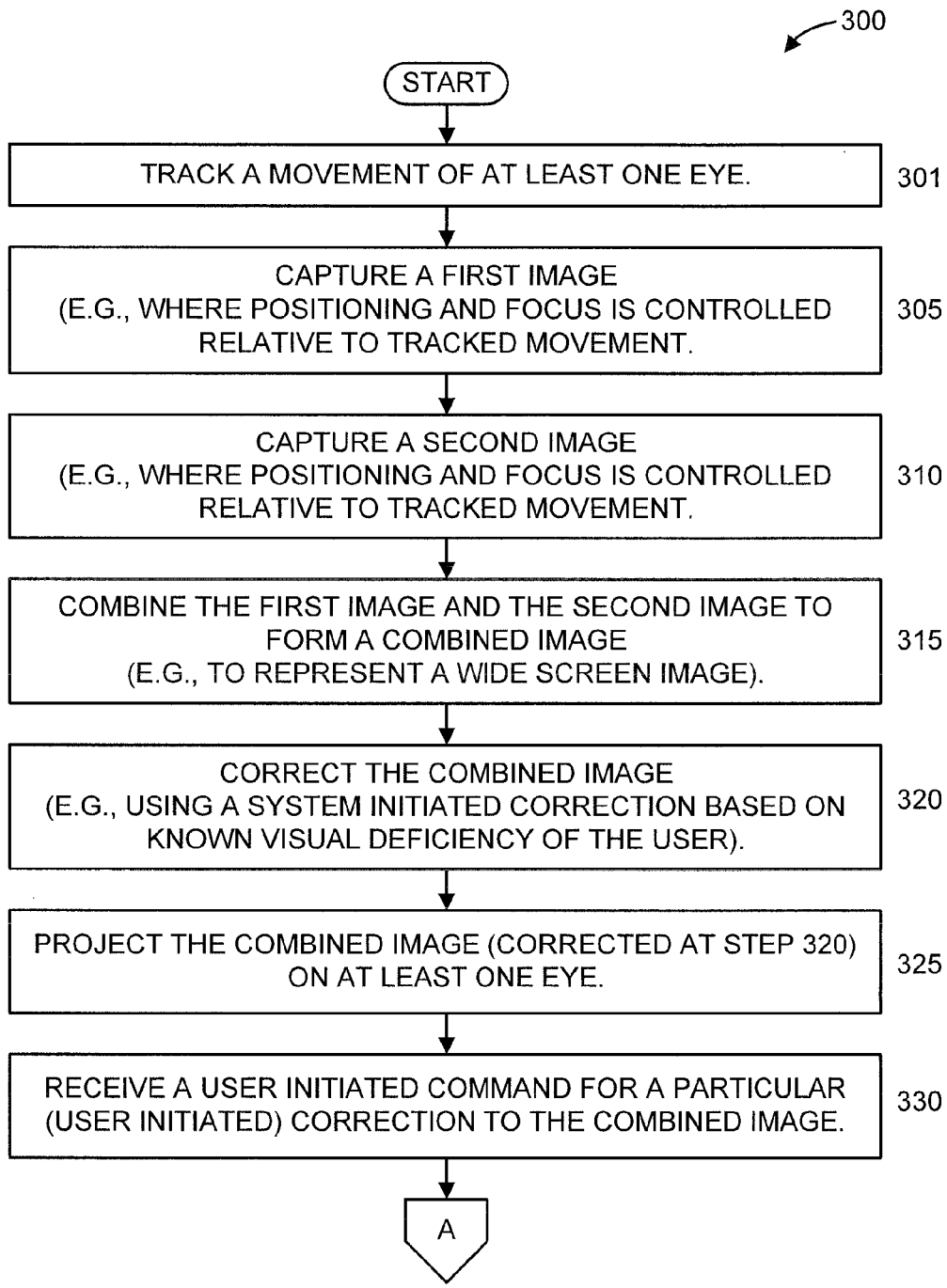
FIGS. 3-4 show an exemplary method 300 for enhancing vision, in accordance with an embodiment of the present principles.
Figure 4:
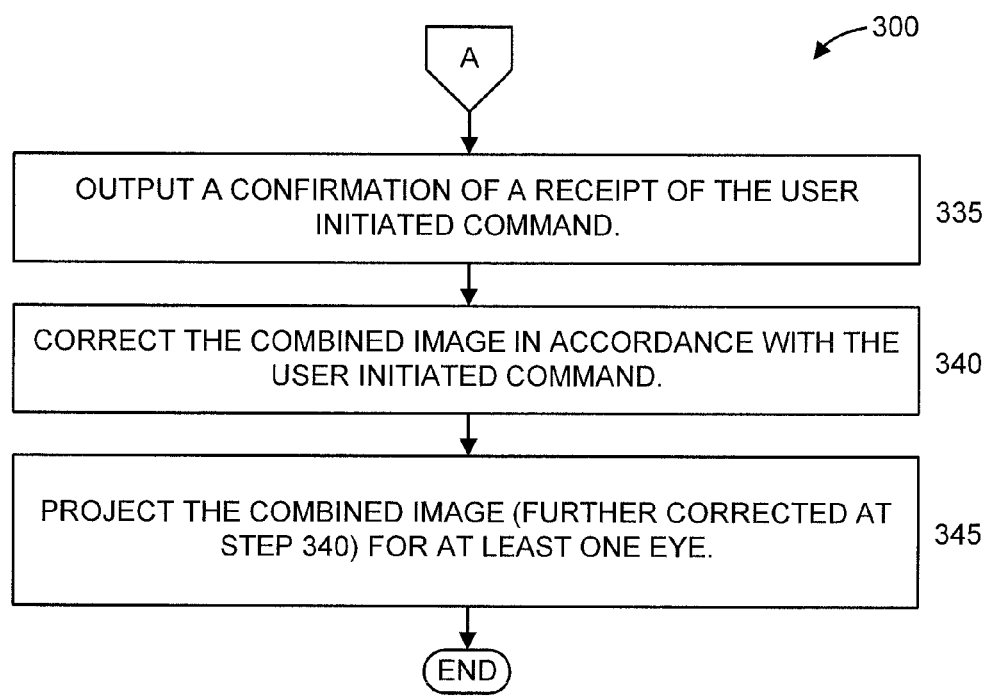
Figure 5:
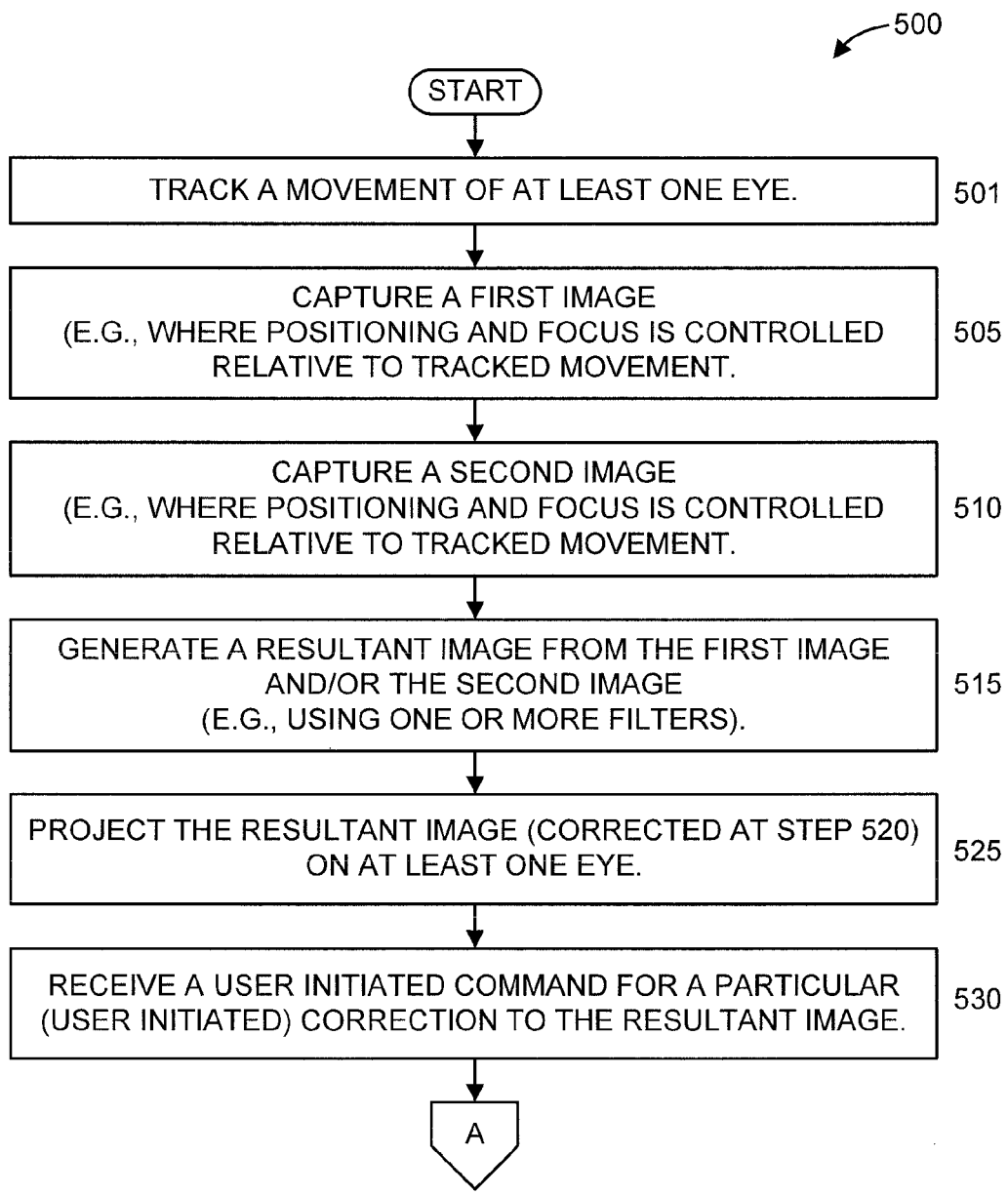
FIGS. 5-6 show another exemplary method 500 for enhancing vision, in accordance with an embodiment of the present principles.
Figure 6:
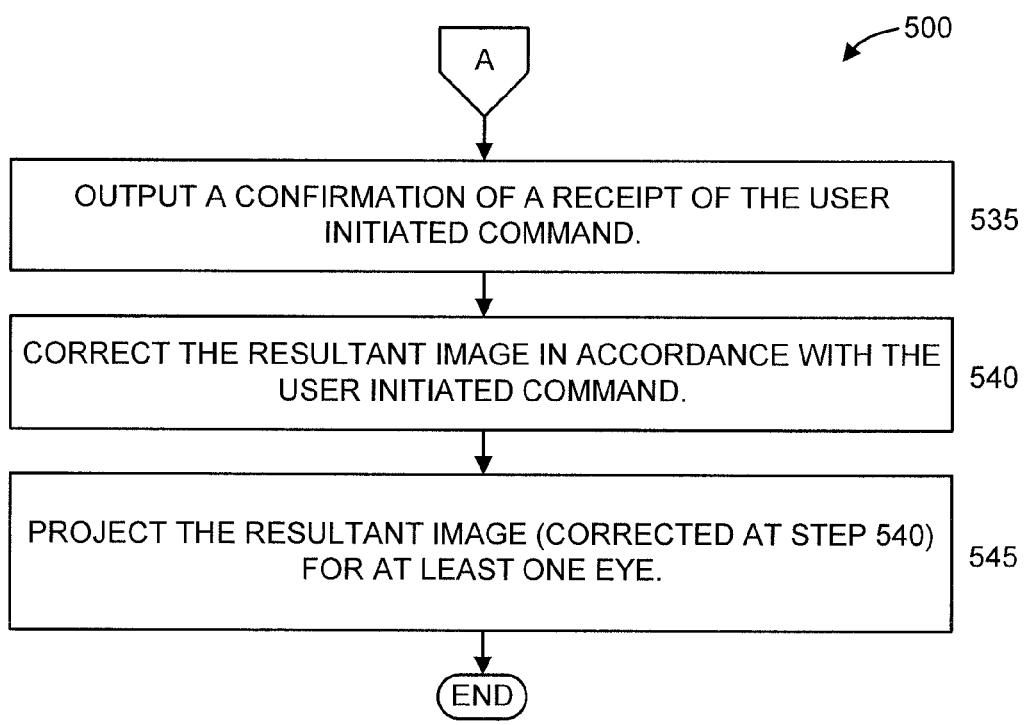

Further, it is to be appreciated that processing system 100 may perform at least part of the method described herein including, for example, at least part of method 300 of FIGS. 3-4 and/or at least part of method 500 of FIGS. 5-6. Similarly, part or all of system 200 may be used to perform at least part of method 300 of FIGS. 3-4 and/or at least part of method 500 of FIGS. 5-6.

FIG. 2 shows an exemplary system 200 for enhancing vision, in accordance with an embodiment of the present principles. The system 200 includes a first camera 210, a second camera 220, an image combiner/generator 230, an image corrector 240, a user input device 250, a user output device 260, an eye tracking device 270, and a wearable image projection device 280.

The eye tracking device 270 can be, and/or otherwise include, a camera such as, for example, the first camera 210 or the second camera 220 or another camera, or a compass, or an accelerometer, or so forth. It is to be appreciated that the preceding eye tracking devices are merely illustrative and, thus, other eye tracking devices can also be used in accordance with the teachings of the present principles, while maintaining the spirit of the present principles.

In the embodiment of system 200, user input device 250 includes a speaker recognition system 250A and a speech recognition system 250B. In an embodiment, the speaker recognition system 250A recognizes the intended user, so that only speech from the intended user is provided to and/or used by the speech recognition system 250B. However, it is to be appreciated that the user input device 250 can be any of, but is not limited to, a microphone, a camera, a mouse, a track pad, a speaker recognition system, a speech recognition system, and so forth. Of course, system 200 can include more than one user input device 250. It is to be appreciated that the preceding user input devices are merely illustrative and, thus, other user input devices can also be used in accordance with the teachings of the present principles, while maintaining the spirit of the present principles.

In the embodiment of system 200, user output device 260 includes a speech synthesis system 260A. The user output device 260 (speech synthesis system 260A) can be used to confirm user commands, ask the user questions to help provide enhanced vision, and so forth. However, it is to be appreciated that the user output device 260 can be any of, but is not limited to, a speaker, a tactile output device, a voice synthesizer, and so forth. Of course, system 200 can include more than one user output device 260. It is to be appreciated that the preceding user output devices are merely illustrative and, thus, other user output devices can also be used in accordance with the teachings of the present principles, while maintaining the spirit of the present principles.

It is to be appreciated that the image combining functions of the image combiner/generator 230 can be bypassed and/or otherwise not used for situations as described with respect to method 500 of FIGS. 5-6.

FIGS. 3-4 show an exemplary method 300 for enhancing vision, in accordance with an embodiment of the present principles.

At step 301, track a movement of at least one eye, by the eye tracking device 270.

At step 305, capture a first image, by the first camera 210. In an embodiment, the first image is captured such that a positioning and focus of the first camera is controlled relative to the tracked movement of the at least one eye as per step 301.

At step 310, capture a second image, by the second camera 220. In an embodiment, the second image is captured such that a positioning and focus of the second camera is controlled relative to the tracked movement of the at least one eye as per step 301.

At step 315, combine the first image and the second image to form a combined image, by the image combiner/generator 230. In an embodiment, the combined image is formed to represent a wide screen image. As used herein, the term "wide screen image" refers to a resultant combined image having a field of view greater than any of the first image any the second image.

At step 320, correct the combined image, by the image corrector 240. In an embodiment, such correction can be, for example, a system initiated correction based upon, for example, a known visual deficiency of the user.

At step 325, project the combined image (corrected by step 320) on at least one eye of the user, by the wearable image projection device 280.

At step 330, receive a user initiated command for a particular (further) correction to the combined image (already corrected by step 320), by the user input device 250. It is to be appreciated that the correction provided at step 330 differs from the correction provided at step 340) in that the correction of step 330 is system initiated (e.g., based on a known visual deficiency of the user) versus the correction of step 340 being user initiated (e.g., based on the user desiring some particular correction based on the image he/she is currently viewing). Moreover, the user command received at step 330 can simply be a selection of possible vision enhancement options presented, and/or otherwise known, to the user. Presentation can be via the projection device 280 or some other device or by knowing that certain keys, inputs, buttons and/or so forth on a user input device 250 represent certain corresponding corrections.

At step 335, output a confirmation of a receipt of the user initiated command, by the user output device 260.

At step 340, correct the combined image in accordance with the user initiated command, by the image corrector 240. Hence, step 340 performs a user controllable adjustment of the combined image.

At step 345, project the combined image (further corrected at step 340, noting the initial system initiated correction at step 320) for at least one eye of a user, by the wearable image projection device 280.

Regarding step 340, a user controllable adjustment performed according to the user initiated command can include, but is not limited to, any of enlarging, reducing, correcting, simplifying, outlining, deconvoluting, contrasting, customizing, compensating, backward S filtering, reducing glare, darkening, and lightening. Further, the user controllable adjustment can include hiding from another eye when the combined image is projected on only one of the at least one eye. Of course, other user controllable adjustments can also be used, given the teachings of the present principles provided herein, while maintaining the spirit of the present principles.

Regarding steps 325 and 345, in an embodiment, the at least one eye will include the good eye, and can further include the affected eye. In another embodiment, the at least one eye will include the affected eye, and can further include the good eye.

An particularly advantageous feature of the present principles is combining video images from the focus field of vision of an eye with diminished or no vision and video images from a normal eye into an enhanced image projected on to the eyeglass lens of a normal eye to achieve an image similar to what would be seen by two normal eyes.

The present principles are especially useful to a person with distorted or blurred vision in one eye or loss of distance vision which could not be corrected by simple surgery or ordinary eyeglasses. This can occur from conditions like macular folding, epiretinal membrane (ERM), damage to a retina, or macular degeneration. Many of these diseases are relatively common conditions in older adults. Advantageously, the present principles would also be useful to patients recovering from surgery for the above conditions because sometimes full vision restoration can take up to a year.

In an embodiment, the present principles could also be used as a safe driving aid for persons with no visual disability. Although cameras and video detection are already built into some new luxury cars, this appliance could be used with any vehicle and could be shared among members of a family (but not simultaneously). In an embodiment, the present principles could be used by bicycle or motorcycle riders, as these vehicles do not ordinarily come with video cameras.

The user could also try to correct vision only in the affected eye without merging both images and using only his/her good eye. This is accomplished by asking the vision enhancing system to improve the image in the affected eye and not to try to combine both images. This feature would be most useful to correct distortion, such as wavy lines. The vision enhancing system, in response, will use various video filters to manipulate the images to the user's specifications.

FIGS. 5-6 show another exemplary method 500 for enhancing vision, in accordance with an embodiment of the present principles.

At step 501, track a movement of at least one eye, by the eye tracking device 270.

At step 505, capture a first image, by the first camera 210. In an embodiment, the first image is captured such that a positioning and focus of the first camera is controlled relative to the tracked movement of the at least one eye as per step 501.

At step 510, capture a second image, by the second camera 220. In an embodiment, the second image is captured such that a positioning and focus of the second camera is controlled relative to the tracked movement of the at least one eye as per step 501.

At step 515, generate an image to be displayed (hereinafter resultant image) from the first image and/or the second image, but without actually combining the first image and the second image into a widescreen image, by the image combiner/generator 580. Such resultant image can be generated using one or more image filters.

At step 525, project the resultant image on the affected eye, by the wearable image projection device 280.

At step 530, receive a user initiated command for a particular (user initiated) correction to the resultant image, by the user input device 250.

At step 535, output a confirmation of a receipt of the user initiated command, by the user output device 260.

At step 540, correct the resultant image in accordance with the user initiated command, by the image corrector 240.

At step 545, project the resultant image (corrected at step 540) for the affected eye of the user, by the wearable image projection device 280.

A description will now be given of some examples of the type of distorted vision common in persons with retinal damage to which the present principles can be applied.

For image processing, deconvolution is the process of approximately inverting the process that caused an image to be blurred. Specifically, unsharp masking is a simple linear image operation involving a convolution by a kernel that is the Dirac delta minus a Gaussian blur kernel. Deconvolution, on the other hand, is generally considered an ill-posed inverse problem that is best solved by nonlinear approaches. While unsharp masking increases the apparent sharpness of an image in ignorance of the manner in which the image was acquired, deconvolution increases the apparent sharpness of an image, but based on information describing some of the likely origins of the distortions of the light path used in capturing the image. Hence, deconvolution may sometimes be preferred, where the cost in preparation time and per-image computation time are offset by the increase in image clarity.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method for enhancing vision, comprising:
capturing a first image by a first camera;
capturing a second image by a second camera;
combining the first image and the second image to form a combined image, the combined image being adjusted according to a user controllable adjustment, the user controllable adjustment being performed responsive to a voice command, and comprising at least one of:
for the at least one eye, at least one of, enlarging, reducing, correcting, simplifying, outlining, deconvoluting, contrasting, customizing, compensating, backward S filtering, reducing glare, darkening, and lightening; and
for only a good eye of the user having a relative vision better than an affected eye of the user, hiding a visual artifact from only the good eye of the user;
tracking a movement of the at least one eye to control a positioning and a focus of the first camera and the second camera;
correcting the combined image by a system initiated correction to form a corrected combined image; and
projecting, using a projector, the corrected combined image directly onto at least one eye of a user, the projector being a wearable image projection device positioned to face the at least one eye of a user,
wherein the corrected combined image represents a wide screen image having a field of view greater than any of the first image and the second image taken individually.

2. The method of claim 1, wherein the first image and the second image are captured based on respective intended focus points of both eyes of the user.

3. The method of claim 1, wherein the at least one eye, on which the combined image is projected, comprises only a good eye of the user, the good eye having a relative vision better than an affected eye of the user.

4. The method of claim 1, wherein the at least one eye, on which the combined image is projected, comprises only an affected eye of the user, the affected eye having a relative vision worse than a good eye of the user.

5. The method of claim 1, wherein the user controllable adjustment is performed responsive to a user touch.

6. A system for enhancing vision, comprising:
a first camera for capturing a first image;
a second camera for capturing a second image;
an image combiner for combining the first image and the second image to form a combined image, the combined image being adjusted according to a user controllable adjustment, the user controllable adjustment being performed responsive to a voice command, and comprising at least one of:
for the at least one eye, at least one of, enlarging, reducing, correcting, simplifying, outlining, deconvoluting, contrasting, customizing, compensating, backward S filtering, reducing glare, darkening, and lightening; and
for only a good eye of the user having a relative vision better than an affected eye of the user, hiding a visual artifact from only the good eye of the user;
tracking a movement of the at least one eye to control a positioning and a focus of the first camera and the second camera;

an image corrector for correcting the combined image by a system initiated correction to form a corrected combined image; and a projector for projecting the corrected combined image directly onto at least one eye of a user, the projector being a wearable image projection device positioned to face the at least one eye of a user, wherein the corrected combined image represents a wide screen image having a field of view greater than any of the first image and the second image taken individually.

7. The system of claim 6, wherein the first image and the second image are captured based on respective intended focus points of both eyes of the user.

8. The system of claim 6, wherein the at least one eye, on which the combined image is projected, comprises at least a good eye of the user, the good eye having a relative vision better than an affected eye of the user.

9. The system of claim 6, wherein the at least one eye, on which the combined image is projected, comprises at least an affected eye of the user, the affected eye having a relative vision worse than a good eye of the user.

10. The system of claim 6, wherein the wearable image projection device is comprised in a pair of eyeglasses.

11. The system of claim 6, wherein the voice command is processed by at least one of a speaker recognition system and a speech recognition system.

12. The system of claim 6, wherein the user controllable adjustment is performed responsive to a user touch.

13. The system of claim 6, further comprising an eye tracking device for tracking a movement of the at least one eye to control a positioning and a focus of the first camera and the second camera.

14. The system of claim 6, further comprising:
a speaker recognition system for recognizing the user;
a speech recognition system for receiving speech commands from the user; and
a speech synthesis system for synthesizing at least one of responses to the speech commands and user-selectable image correction options,
wherein only speech identified by the speaker recognition system as being provided by the user is acted upon by the speech recognition system.

* * * * *